(12) United States Patent
Vogel et al.

(10) Patent No.: US 8,491,623 B2
(45) Date of Patent: Jul. 23, 2013

(54) ATRAUMATIC OCCLUSION BALLOONS AND SKIRTS, AND METHODS OF USE THEREOF

(75) Inventors: Jean-Marie Vogel, Lincoln, MA (US); William E. Cohn, Bellaire, TX (US)

(73) Assignee: Pluromed, Inc., Woburn, MA (US)

( * ) Notice: Subject to any disclaimer, the term of this patent is extended or adjusted under 35 U.S.C. 154(b) by 1038 days.

(21) Appl. No.: 11/851,848

(22) Filed: Sep. 7, 2007

(65) Prior Publication Data
US 2008/0215036 A1 Sep. 4, 2008

Related U.S. Application Data

(60) Provisional application No. 60/843,601, filed on Sep. 11, 2006.

(51) Int. Cl.
*A61M 29/00* (2006.01)
(52) U.S. Cl.
USPC ............ 606/200; 606/108; 606/127; 606/159
(58) Field of Classification Search
USPC .................. 623/1.11; 606/108, 127, 200, 159
See application file for complete search history.

(56) References Cited

U.S. PATENT DOCUMENTS

| | | |
|---|---|---|
| 3,889,685 A | 6/1975 | Miller, Jr. et al. |
| 4,168,708 A | 9/1979 | Lepley, Jr. et al. |
| 4,188,373 A | 2/1980 | Krezanoski |
| 4,474,751 A | 10/1984 | Haslam et al. |
| 4,478,822 A | 10/1984 | Haslam et al. |
| 4,708,140 A | 11/1987 | Baron |
| 4,834,091 A | 5/1989 | Ott |
| 4,946,463 A | 8/1990 | Wright |
| 5,523,492 A | 6/1996 | Emanuele et al. |
| 5,567,859 A | 10/1996 | Emanuele et al. |
| 5,696,298 A | 12/1997 | Emanuele et al. |
| 5,797,877 A | 8/1998 | Hamilton et al. |
| 5,800,711 A | 9/1998 | Reeve et al. |
| 6,547,804 B2 | 4/2003 | Porter et al. |
| 6,761,824 B2 | 7/2004 | Reeve et al. |

(Continued)

FOREIGN PATENT DOCUMENTS

| | | |
|---|---|---|
| WO | WO-92/16484 | 10/1992 |
| WO | WO-01/85845 | 11/2001 |
| WO | WO-2004/084703 | 10/2004 |

OTHER PUBLICATIONS

Boodwhani, M., et al. "Safety and Efficacy of a Novel Gel for Vascular Occlusion in Off-Pump Surgery." *Ann Thorac Surg* 2005, 80, 2333-7.

(Continued)

*Primary Examiner* — Gary Jackson
*Assistant Examiner* — Kevin Everage
(74) *Attorney, Agent, or Firm* — Hamilton, Brook, Smith & Reynolds, P.C.

(57) ABSTRACT

One aspect of the present invention relates to catheters that can be placed in or around bodily conduits to occlude or widen a biological lumen without imparting significant trauma to the lumen. In certain embodiments, the invention particularly relates to the use of a polymer composition which can be made to gel upon insertion into said balloon or skirt. In certain embodiments, the inflating viscous polymer composition is a liquid at room temperature and a gel at mammalian physiological temperature. In certain embodiments, the inflating viscous polymer composition comprises an optionally purified inverse thermosensitive polymer.

22 Claims, 6 Drawing Sheets

U.S. PATENT DOCUMENTS

| | | | |
|---|---|---|---|
| 6,977,045 | B2 | 12/2005 | Reeve et al. |
| 2005/0008610 | A1* | 1/2005 | Schwarz et al. ............. 424/78.1 |
| 2005/0147585 | A1 | 7/2005 | Schwarz |
| 2006/0182913 | A1 | 8/2006 | Bertolino et al. |
| 2006/0184048 | A1* | 8/2006 | Saadat ......................... 600/478 |
| 2006/0184112 | A1 | 8/2006 | Horn et al. |

OTHER PUBLICATIONS

Bromberg, L.E., et al. "Temperature-responsive gels and thermogelling polymer matrices for protein and peptide delivery." *Adv Drug Deliv Rev.* May 4, 1998; 31(3): 197-221.

Cabana A, et al. "Study of the gelation process of polyethylene oxide. polypropylene oxide-polyethylene oxide copolymer (poloxamer 407 aqueous solutions." *Journal of Colloid and Interface Science* 1997, 190, 307-312.

Joseph, N., et al. "Angioplasty-related iliac artery rupture: treatment by temporary balloon occlusion." Cardiovasc Intervent Radiol 1987; 10(5):276-9.

Labropoulos, N., et al.; "Complications of the balloon assisted percutaneous transluminal angioplasty." Review article. J Cardiovasc Surg (Torino). Dec. 1994; 35(6):475-89.

March, K. L., et al. "Pharmacokinetics of adenoviral vector-mediated gene delivery to vascular smooth muscle cells: modulation by poloxamer 407 and implication for cardiovascular gene therapy." *Hum Gene Therapy* 1995, 6, 41-53.

Matsuoka, S., et al. "Temporary percutaneous aortic balloon occlusion to enhance fluid resuscitation prior to definitive embolization of posttraumatic liver hemorrhage." Cardiovasc Intervent Radiol Jul.-Aug. 2001; 24(4):274-6.

Qiu and Park; "Environment-sensitive hydrogels for drug delivery." *Adv Drug Deliv Rev.* Dec. 31, 2001; 53(3), 321-339.

Raymond, J., et al. "Temporary vascular occlusion with poloxamer 407." *Biomaterials* 2004, 25, 3983.

Saab, M. A. "Applications of High-Pressure Balloons in the Medical Device Industry," Advanced Polymers, Inc. (1999).

Wainwright, C.L., et al. "Inflammation as a key event in the development of neointima following vascular balloon injury." Clin Exp Pharmacol Physiol. Nov. 2001; 28(11):891-5.

Applications for Medical Balloons [online]. Advanced Polymers Incorporated, 2007 [retrieved on Nov. 28, 2008]. Retrieved from the Internet: <URL: www.advpoly.com/Products/MedicalBalloons/Applications/Default.aspx>.

* cited by examiner

Figure 2

| Sample | $M_w$ | $M_n$ | $M_w/M_n$ | Unsaturation MEq/g | Weight % oxyethylene | Viscosity, centipoise* |
|---|---|---|---|---|---|---|
| Poloxamer 407 | 11,996 | 9,979 | 1.20 | 0.048 | 73.2 | 275,000 |
| Poloxamer 407, lot 00115001, fractionated | 13,551 | 12,775 | 1.06 | 0.005 | 69.3 | > 820,000 |

[A]

| polymer | concentration | temperature |
|---|---|---|
| Tetronic 1107 | 25 w% | 27 °C |
| Tetronic 1107 | 20 w% | 34 °C |
| Purified Tetronic 1107 | 25 w% | 22 °C |
| Purified Tetronic 1107 | 20 w% | 32.5 °C |
| Tetronic 1307 | 25 w% | 24.5 °C |
| Tetronic 1307 | 20 w% | 31 °C |
| Purified Tetronic 1307 | 25 w% | 20 °C |
| Purified Tetronic 1307 | 20 w% | 26 °C |
| Pluronic F108 | 25 w% | 26 °C |
| Pluronic F108 | 20 w% | 60 °C |
| Purified Pluronic F108 | 25 w% | 19 °C |
| Purified Pluronic F108 | 20 w% | 26 °C |

[B]

ATRAUMATIC OCCLUSION BALLOONS AND SKIRTS, AND METHODS OF USE THEREOF

RELATED APPLICATIONS

This application claims the benefit of priority to the filing date of U.S. Provisional Patent Application Ser. No. 60/843,601, filed Sep. 11, 2006.

BACKGROUND OF THE INVENTION

Mammalian (e.g., human) bodies include various lumen, such as arteries, other blood vessels and bodily cavities. The mammalian lumen, such as a coronary artery, sometimes become constricted or blocked, for example, by plaque or a tumor. A constricted passageway may be widened using an angioplasty procedure using a catheter, which includes a balloon carried by a catheter shaft. Additionally, it may be medically desirable to occlude temporarily or permanently a biological lumen to diagnose or treat an ailment. Such an occlusion may also be realized through the use of a catheter.

Unfortunately, the pressure needed to use a balloon to open or occlude a biological lumen may itself cause injury. For example, in the case of arteries, inflated balloons are known to cause dilation of the artery and the resulting injury to the intima can lead to thickening and narrowing of the artery (Wainwright C L, Miller A M, Wadsworth R M. "Inflammation as a key event in the development of neointima following vascular balloon injury," *Clin. Exp. Pharmacol. Physiol.* 2001, 28(11), 891-5; and Labropoulos N, Giannoukas A D, Volteas S K, al Kutoubi A. "Complications of the balloon assisted percutaneous transluminal angioplasty," *J. Cardiovasc. Surg.* (*Torino*) 1994, 35(6), 475-89). Consequently, there is a need for improved methods for using catheters to widen or occlude biological passageways without injuring the lumen. The present invention addresses this need and others.

SUMMARY OF THE INVENTION

One aspect of the present invention relates to catheters that can be placed in or around bodily conduits to occlude or widen a biological lumen without imparting significant trauma to the lumen. Typically, catheters have a balloon or skirt fastened to at least one end around the exterior of a hollow catheter shaft. The hollow interior of the balloon or skirt is in fluid flow relation with the hollow interior of the shaft. The shaft then may be used to provide a fluid supply for inflating the balloon or deploying the skirt.

In certain embodiments, the invention particularly relates to the use of a polymer composition which can be made to gel upon insertion into said balloon or skirt. In certain embodiments, the inflating viscous polymer composition is a liquid at room temperature and a gel at mammalian physiological temperature. In certain embodiments, the inflating viscous polymer composition comprises an optionally purified inverse thermosensitive polymer.

The present invention has a number of advantages over traditional fluid-filled balloons. For example, by using a polymer composition, the reduced need for pressure allows the use of thinner or flimsier materials that better conform to the shape of the lumen wherein the balloon or skirt is deployed. In addition, since the present invention can better conform to the target lumen, it can be used in a wider range of diagnostic and therapeutic applications. Because the firmness of the balloon is not due to internal pressure, a full balloon may not be necessary to achieve occlusion of the lumen. Also sufficient in many instances will be an open structure in the shape or the form of an umbrella (e.g., a skirt) filled with an aforementioned polymer composition.

BRIEF DESCRIPTION OF THE FIGURES

FIG. 2 depicts [A] a table showing the results of the purification of poloxamer 407 (wherein a "*" indicates a viscosity of a 25% solution measured at 30° C. using a cone and plate viscometer); and [B] a table of the gelation temperature of selected reverse phase media in saline.

DETAILED DESCRIPTION OF THE INVENTION

Definitions

Figure 1:
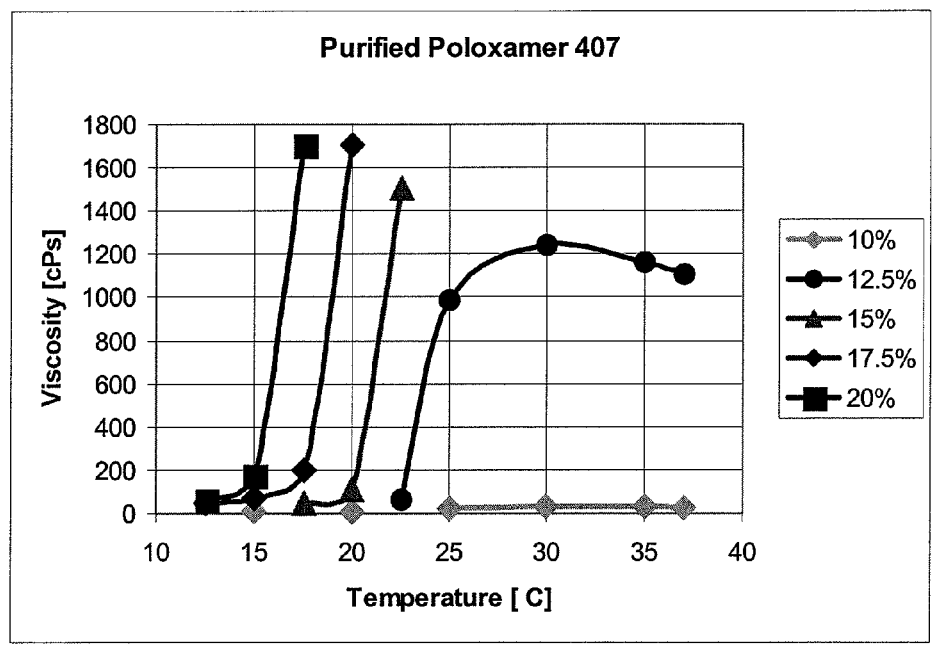
FIG. 1 depicts a graph of viscosity as a function of temperature for various solutions of purified poloxamer 407.
Figure 3:
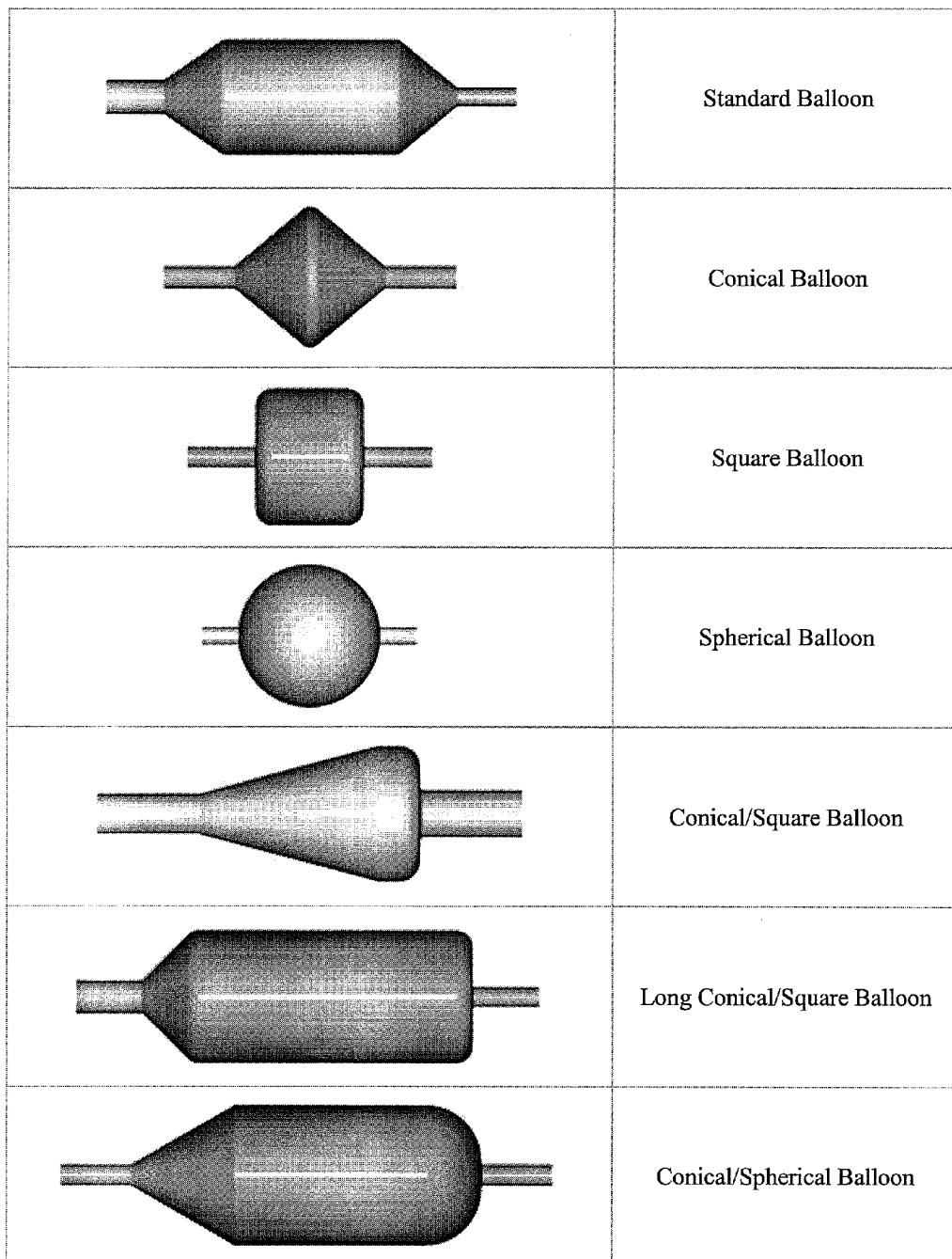
FIG. 3 shows selected balloon shapes of the invention.
Figure 4:
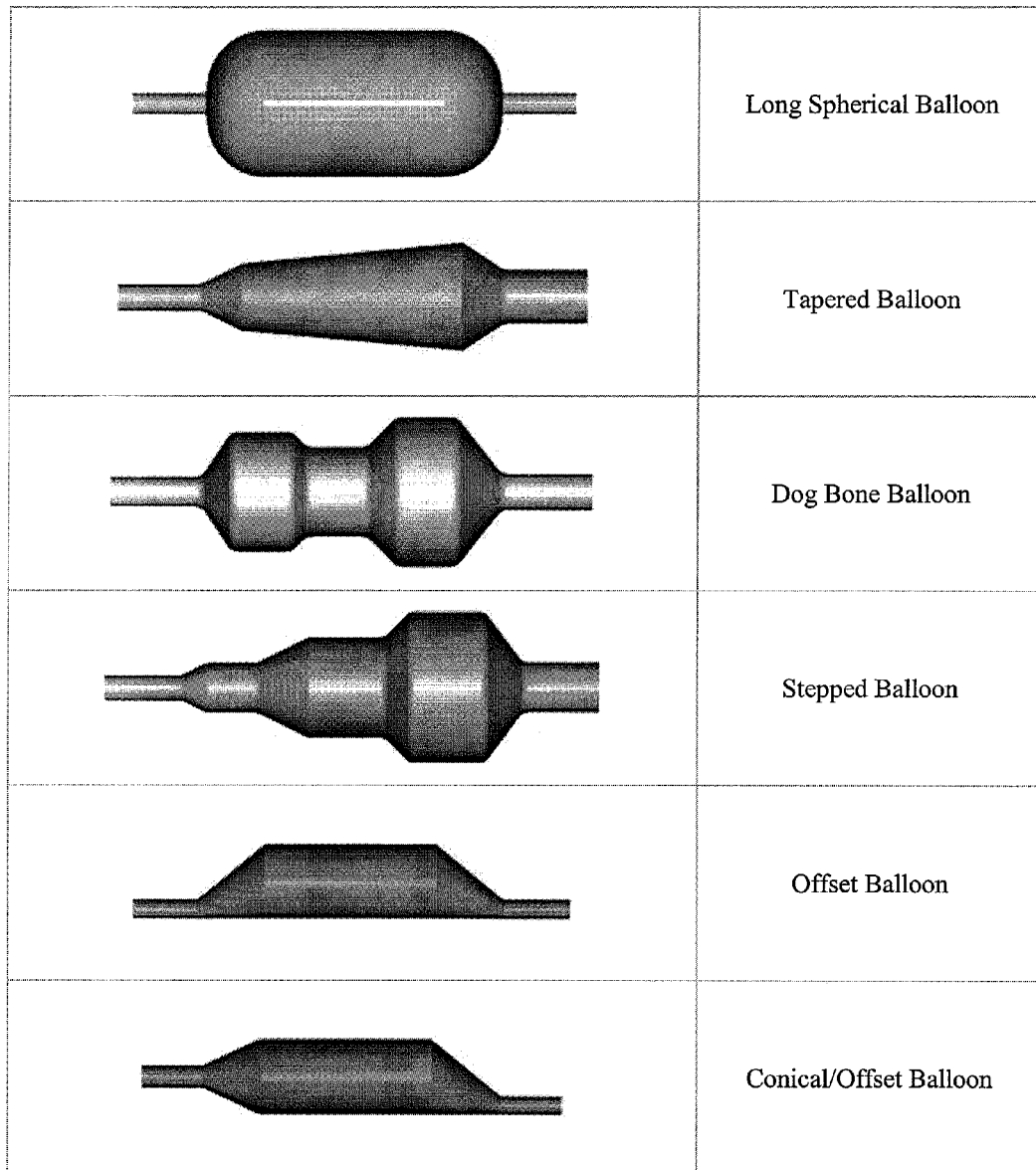
FIG. 4 shows additional selected balloon shapes of the invention.

For convenience, before further description of the present invention, certain terms employed in the specification, examples, and appended claims are collected here. These definitions should be read in light of the remainder of the disclosure and understood as by a person of skill in the art.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The term "anastomosis" as used herein refers to a surgical connection between tubular structures, such as blood vessels. "Beating heart" bypass surgeries, also known as "off-pump" bypass surgeries, are examples of surgical procedures in which anastomoses are performed.

The term "ischemia" as used herein refers to a lack of blood supply (and thus oxygen) to an organ or tissue.

The term "ischemic preconditioning" as used herein refers to a technique in which tissue is rendered resistant to the deleterious effects of prolonged ischemia by prior exposure to brief, repeated periods of vascular occlusion.

Figure 5:
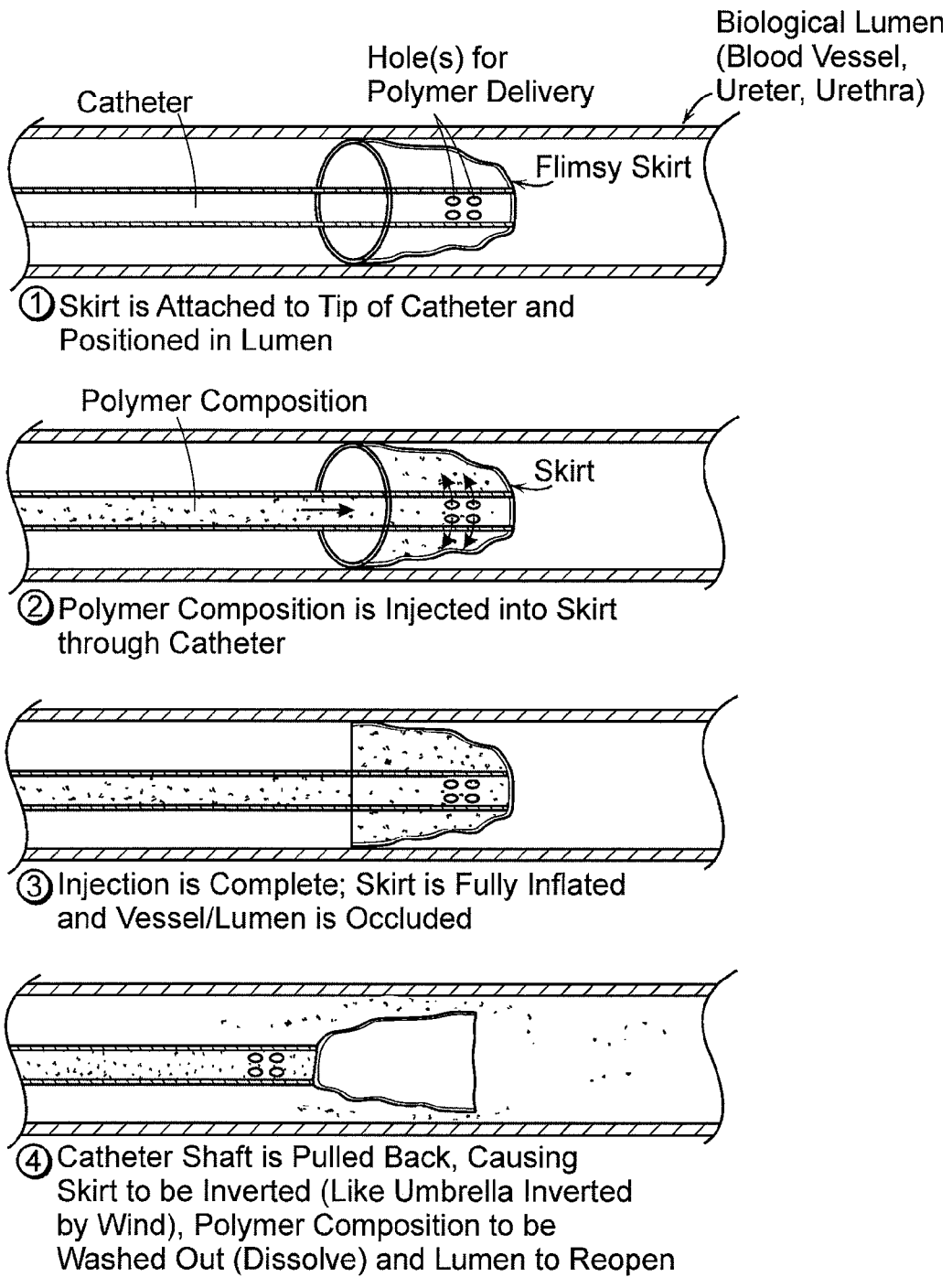
FIG. 5 shows a shirt shape of the invention.
Figure 6:
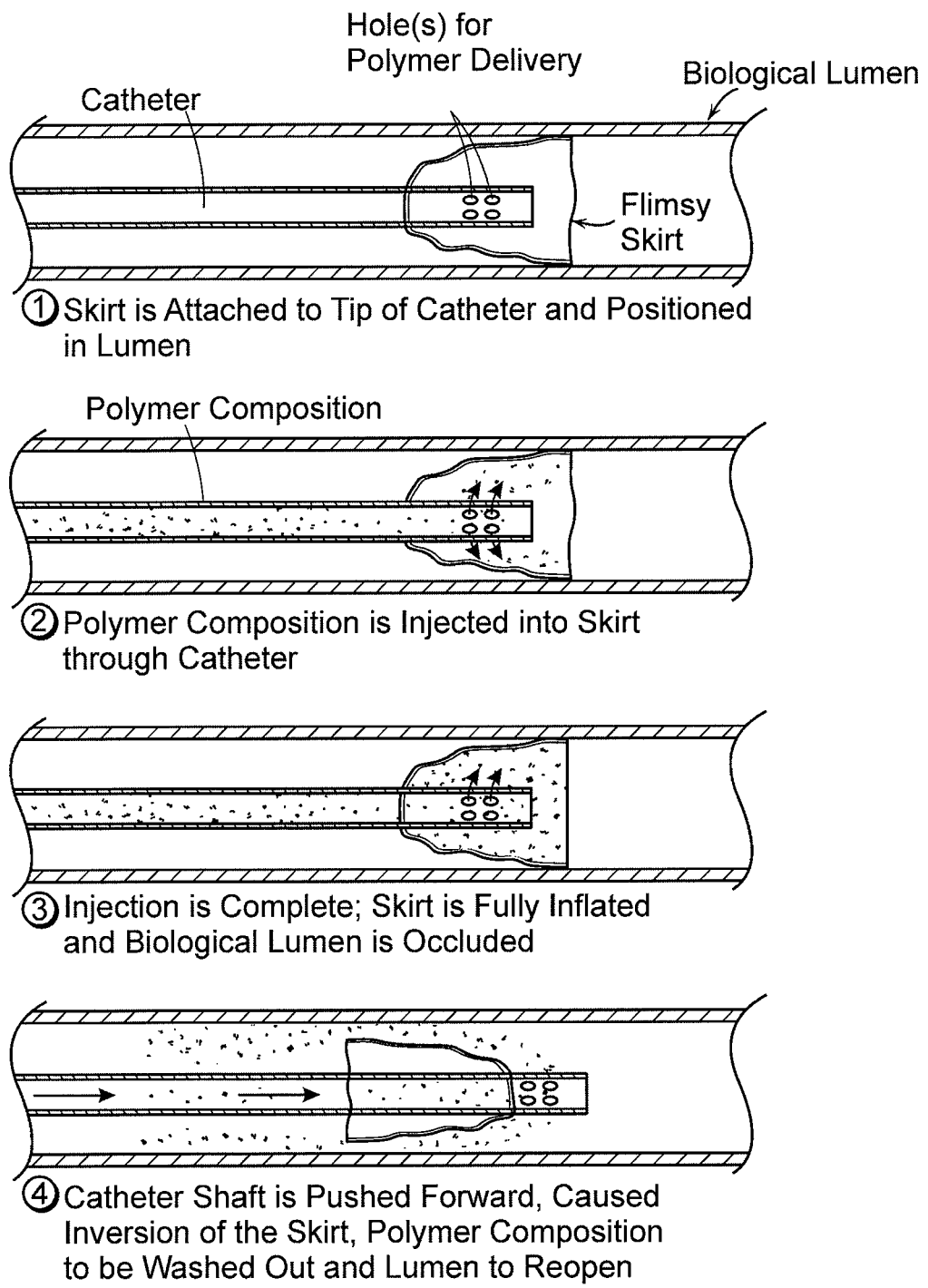
FIG. 6 shows a shirt shape of the invention.

The term "balloon" as used herein refers to non-compliant balloons, semi-compliant balloons and compliant balloons. "Skirts," as used herein, refer to what looks like a half balloon or an umbrella. Skirts can be convex or concave with respect to the catheter. See FIGS. 5 (convex) and 6 (concave).

The term "lumen" denotes the space enclosed by a tube-like structure or hollow organ, such as inside an artery, a vein, a kidney, a gall bladder, a ureter, a urinary bladder, a pancreas, a salivary gland, a colon, a small intestine or a large intestine (i.e., an opening, space, or cavity in a biological system). Lumen, as used herein, encompasses both natural lumen (as described above) and unnatural lumen (such as gun shot wounds or lacerations). Importantly, as used herein, lumen refers to the passageways that connect organs and the organs themselves.

The term "contrast-enhancing" refers to materials capable of being monitored during injection into a mammalian subject by methods for monitoring and detecting such materials, for example by radiography or fluoroscopy. An example of a contrast-enhancing agent is a radiopaque material. Contrast-enhancing agents including radiopaque materials may be either water soluble or water insoluble. Examples of water soluble radiopaque materials include metrizamide, iopamidol, iothalamate sodium, iodomide sodium, and meglumine. Examples of water insoluble radiopaque materials include metals and metal oxides such as gold, titanium, silver, stainless steel, oxides thereof, aluminum oxide, zirconium oxide, etc.

As used herein, the term "polymer" means a molecule, formed by the chemical union of two or more oligomer units. The chemical units are normally linked together by covalent linkages. The two or more combining units in a polymer can be the same, in which case the polymer is referred to as a homopolymer. They can be also be different and, thus, the polymer will be a combination of the different units; these polymers are referred to as copolymers.

As used herein, "crosslinking" is when individual polymer chains are linked together by covalent bonds ("chemical crosslinking") or ionic bonds ("ionic crosslinking") to form a three dimensional network. In certain polymers this kind of process has the effect of producing a gel.

As used herein, the term "inverse thermosensitive polymer" indicates polymers which become more viscous at body temperature, but less viscous at cooler temperature. In certain embodiments it refers to a polymer that is soluble in water at ambient temperature, but at least partially phase-separates out of water at physiological temperature. Inverse thermosensitive polymers include, for example, poloxamer 407, poloxamer 188, Pluronic® F127, Pluronic® F68, poly(N-isopropylacrylamide), poly(methyl vinyl ether), poly(N-vinylcaprolactam); and certain poly(organophosphazenes). See, for example, Lee, B H et al. "Synthesis and Characterization of Thermosensitive Poly(organophosphazenes) with Methoxy-Poly(ethylene glycol) and Alkylamines as Side Groups," *Bull. Korean Chem. Soc.* 2002, 23, 549-554.

The terms "reversibly gelling" and "inverse thermosensitive" refer to the property of a inverse thermosensitive polymers wherein gelation takes place upon an increase in temperature, rather than a decrease in temperature.

The term "transition temperature" refers to the temperature or temperature range at which gelation of an inverse thermosensitive polymers occurs.

The phrase "polydispersity index" refers to the ratio of the "weight average molecular weight" to the "number average molecular weight" for a particular polymer; it reflects the distribution of individual molecular weights in a polymer sample.

The phrase "weight average molecular weight" refers to a particular measure of the molecular weight of a polymer. The weight average molecular weight is calculated as follows: determine the molecular weight of a number of polymer molecules; add the squares of these weights; and then divide by the total weight of the molecules.

The phrase "number average molecular weight" refers to a particular measure of the molecular weight of a polymer. The number average molecular weight is the common average of the molecular weights of the individual polymer molecules. It is determined by measuring the molecular weight of n polymer molecules, summing the weights, and dividing by n.

The term "biocompatible", as used herein, refers to having the property of being biologically compatible by not producing a toxic, injurious, or immunological response in living tissue.

The term "poloxamer" denotes a symmetrical block copolymer, consisting of a core of PPG polyoxyethylated to both its terminal hydroxyl groups, i.e., conforming to the interchangable generic formula $(PEG)_X$-$(PPG)_Y$-$(PEG)_X$ and $(PEO)_X$-$(PPO)_Y$-$(PEO)_X$. Each poloxamer name ends with an arbitrary code number, which is related to the average numerical values of the respective monomer units denoted by X and Y.

The term "poloxamine" denotes a polyalkoxylated symmetrical block copolymer of ethylene diamine conforming to the general type $[(PEG)_X$-$(PPG)_Y]_2$—$NCH_2CH_2N$-$[(PPG)_Y$-$(PEG)_X]_2$. Each Poloxamine name is followed by an arbitrary code number, which is related to the average numerical values of the respective monomer units denoted by X and Y.

"Alginic acid" as used here in is a naturally occurring hydrophilic colloidal polysaccharide obtained from the various species of brown seaweed (*Phaeophyceae*). It occurs in white to yellowish brown filamentous, grainy, granular or powdered forms. It is a linear copolymer consisting mainly of residues of β-1,4-linked D-mannuronic acid and α-1,4-linked L-glucuronic acid. These monomers are often arranged in homopolymeric blocks separated by regions approximating an alternating sequence of the two acid monomers, as shown below:

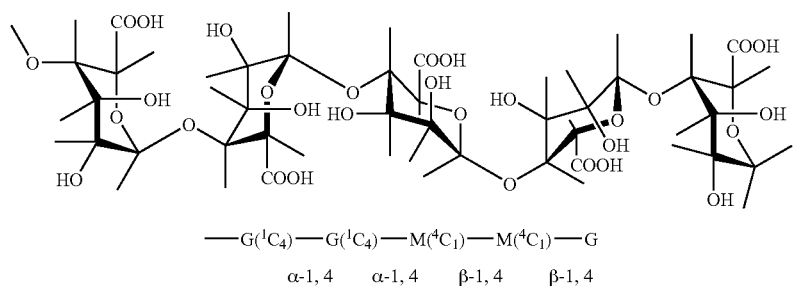

$$—G(^1C_4)—G(^1C_4)—M(^4C_1)—M(^4C_1)—G$$
$$\alpha\text{-1,4} \quad \alpha\text{-1,4} \quad \beta\text{-1,4} \quad \beta\text{-1,4}$$

The formula weight of the structural unit is 176.13 (theoretical; 200 is the actual average). The formula weight of the macromolecule ranges from about 10,000 to about 600,000 (typical average).

"Sodium alginate" and "potassium alginate" are salts of alginic acid. For example, "potassium alginate" is shown below:

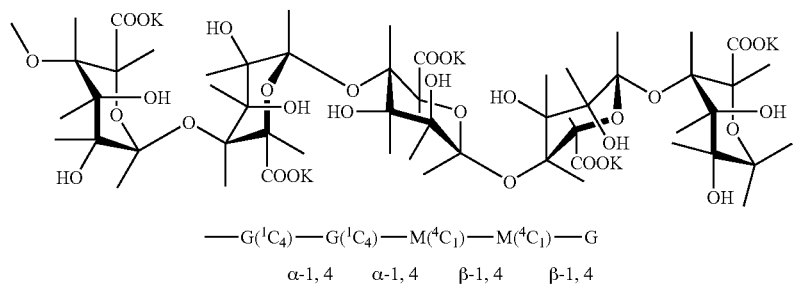

$$—G(^1C_4)—G(^1C_4)—M(^4C_1)—M(^4C_1)—G$$
$$\alpha\text{-1,4} \quad \alpha\text{-1,4} \quad \beta\text{-1,4} \quad \beta\text{-1,4}$$

"Gellan gum" is a high molecular weight polysaccharide gum produced by a pure culture fermentation of a carbohydrate by *Pseudomonas elodea*, purified by recovery with isopropyl alcohol, dried, and milled. The high molecular weight polysaccharide is principally composed of a tetrasaccharide repeating unit of one rhamnose, one glucuronic acid, and two glucose units, and is substituted with acyl (glyceryl and acetyl) groups as the O-glycosidically-linked esters. The glucuronic acid is neutralized to a mixed potassium, sodium, calcium, and magnesium salt. It usually contains a small amount of nitrogen containing compounds resulting from the fermentation procedures. It has a formula weight of about 500,000. "Sodium gellan" and "potassium gellan" are salts of gellan gum.

Carboxymethylcellulose (CMC) is a polymer derived from natural cellulose. Unlike cellulose, CMC is highly water-soluble. The CMC structure is based on the β-(1-4)-D-glucopyranose polymer of cellulose. Different preparations may have different degrees of substitution, but it is generally in the range of about 0.6 to about 0.95 derivatives per monomer unit, as shown below:

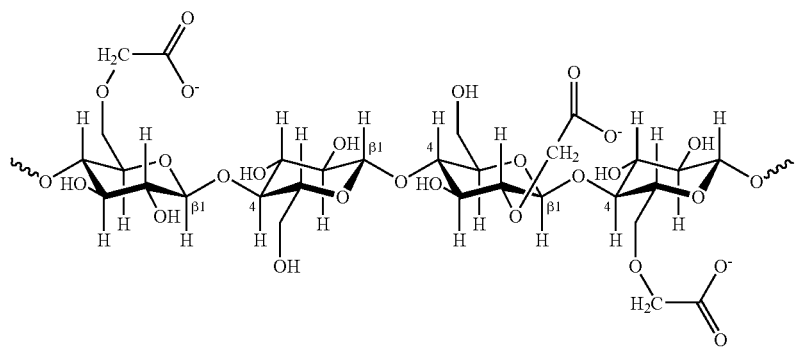

CMC molecules are somewhat shorter, on average, than native cellulose with uneven derivatization giving areas of high and low substitution. This substitution is mostly 2-O- and 6-O-linked, followed in order of importance by 2,6-di-O- then 3-O-, 3,6-di-O-, 2,3-di-O- lastly 2,3,6-tri-O-linked. It appears that the substitution process is a slightly cooperative (within residues) rather than random process giving slightly higher than expected unsubstituted and trisubstituted areas. CMC molecules are most extended (rod-like) at low concentrations but at higher concentrations the molecules overlap and coil up and then, at high concentrations, entangle to become a thermoreversible gel. Increasing ionic strength and reducing pH both decrease the viscosity as they cause the polymer to become more coiled. The average chain length and degree of substitution are of great importance; the more-hydrophobic lower substituted CMCs are thixotropic but more-extended higher substituted CMCs are pseudoplastic. At low pH, CMC may form cross-links through lactonization between carboxylic acid and free hydroxyl groups.

"Poly vinyl alcohol" (PVA) is a water soluble polymer synthesized by hydrolysis of a poly vinyl ester such as the acetate and used for preparation of fibers. PVA is a thermoplastic that is produced from full or partial hydrolysis of vinyl ester such as vinyl acetate resulting in the replacement of some or all of the acetyl groups with hydroxyl groups. For example:

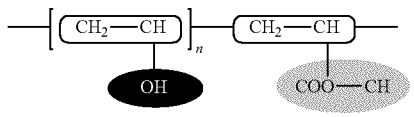

In certain embodiments polyvinyl alcohol (PVA) is a synthetic resin produced by polymerisation of vinyl acetate (VAM) followed by hydrolysis of the polyvinyl acetate (PVAc) polymer. The degree of polymerisation determines the molecular weight and viscosity in solution. The degree of hydrolysis (saponification) signifies the extent of conversion of the polyvinyl acetate to the polyvinyl alcohol For example n (degree of hydrolysis) may be in the range of about 68.2 to about 99.8 mol. % and the MW (weight average molecular weight) may range from about 10,000 to about 190,000.

Hyaluronic acid (HA) is a polymer composed of repeating dimeric units of glucuronic acid and N-acetyl glucosamine. It may be of extremely high molecular weight (up to several million daltons) and forms the core of complex proteoglycan aggregates found in extracellular matrix. HA is comprised of linear, unbranching, polyanionic disaccharide units consisting of glucuronic acid (GlcUA) an N-acetyl glucosamine (GlcNAc) joined alternately by β-1-3 and β-1-4 glycosidic bonds (see below). It is a member of the glycosaminoglycan family which includes chondroitin sulphate, dermatin sulphate and heparan sulphate. Unlike other members of this family, it is not found covalently bound to proteins.

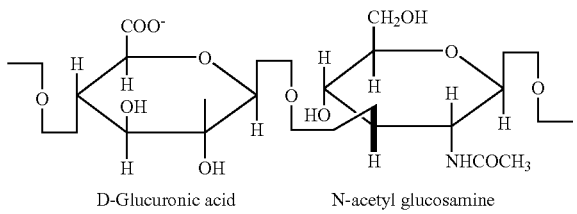

When incorporated into a neutral aqueous solution hydrogen bond formation occurs between water molecules and adjacent carboxyl and N-acetyl groups. This imparts a conformational stiffness to the polymer, which limits its flexibility. The hydrogen bond formation results in the unique water-binding and retention capacity of the polymer. It also follows that the water-binding capacity is directly related to the molecular weight of the molecule. Up to six liters of water may be bound per gram of HA.

HA solutions are characteristically viscoelastic and pseudoplastic. This rheology is found even in very dilute solutions of the polymer where very viscous gels are formed. The viscoelastic property of HA solutions which is important in its use as a biomaterial is controlled by the concentration and molecular weight of the HA chains. The molecular weight of HA from different sources is polydisperse and highly variable ranging from $10^4$ to $10^7$ Da. The extrusion of HA through the cell membrane as it is produced permits unconstrained polymer elongation and hence a very high molecular weight molecule.

The term "degradable", as used herein, refers to having the property of breaking down or degrading under certain conditions, e.g., by dissolution.

Contemplated equivalents of the polymers, subunits and other compositions described above include such materials which otherwise correspond thereto, and which have the same general properties thereof (e.g., form inverse thermosensitive polymer compositions), wherein one or more simple variations of substituents are made which do not adversely affect the efficacy of such molecule to achieve its intended purpose. In general, the compositions of the present invention may be prepared by, for example, described below, or by modifications thereof, using readily available starting materials, reagents and conventional synthesis procedures. In these reactions, it is also possible to make use of variants which are in themselves known, but are not mentioned here.

Selected Polymer Compositions of the Invention

In certain embodiments, the polymers used in the inventive methods gel by one or more physical phenomena, such as temperature, pH changes and/or ionic interactions. In certain embodiments, the polymers used in a method of the invention are crosslinkable polymers. Also, the polymer compositions of the invention can include one or more additives; for example, contrast agents may be added to the inverse thermosensitive polymers.

In certain embodiments, the polymer composition of the invention may be a flexible or flowable material. By "flowable" is meant the ability to assume, over time and at body temperature, the shape of the space into which the composition or material is introduced. Also encompassed by the term "flowable" are highly viscous, gel-like materials at room temperature that may be delivered into the balloon by being injected with any one of the commercially available power injection devices that provide injection pressures greater than would be exerted by manual means alone. When the polymer used is itself flowable, the polymer composition of the invention, even when viscous, need not include a biocompatible solvent to be flowable, although trace or residual amounts of biocompatible solvents may be present.

In one embodiment, two solutions—a polymer solution and a crosslinker solution—are injected separately (e.g., through a dual lumen catheter) into a balloon or skirt wherein they form a gel. In a related embodiment, two solutions are mixed just prior to injection. Said polymer solutions may comprise an anionic polymer, a cationic polymer or a non-ionically crosslinkable polymer. Such polymers may be selected from one or more of the following: alginic acid, sodium alginate, potassium alginate, sodium gellan, potassium gellan, carboxy methyl cellulose, hyaluronic acid, and polyvinyl alcohol. The cross-linking of the polymer may be achieved with anionic crosslinking ions, cationic crosslinking ions, or non-ionic crosslinking agents. Crosslinking agents include, but are not limited to, one or more of the following: phosphate, citrate, borate, succinate, maleate, adipate, oxalate, calcium, magnesium, barium and strontium. Exemplary pairings of polymers and crosslinkers include anionic polymer monomers with cations, such as, for example, alginates with calcium, barium or magnesium; gellans with calcium, magnesium or barium; or hyaluronic acid with calcium. An example of an exemplary pairing of a non-ionic polymer with a chemical crosslinking agent is a polyvinyl alcohol with borate (at a slightly alkaline pH).

In addition, in certain embodiments, the polymer composition of the invention may be formed from an aqueous solution of inverse thermosensitive polymers. These polymer solutions are liquids below body temperature and gel at about body temperature. The polymer solution is prepared external of the body, i.e., at a temperature below body temperature. The polymer solution may be further chilled to prolong the time the gel stays in the liquid form upon introduction into the body. A preferred temperature is about 10° C. below the gelation temperature of the polymer solution.

In general, the inverse thermosensitive polymers used in the methods of the invention can be administered in a liquid form. The material, upon reaching body temperature, undergoes a transition from a liquid to a gel. In certain embodiments, the inverse thermosensitive polymers used in connection with the methods of the invention may comprise a block copolymer with inverse thermal gelation properties. The block copolymer can further comprise a polyoxyethylene-polyoxypropylene block copolymer, such as a biodegradable, biocompatible copolymer of polyethylene oxide and polypropylene oxide.

In certain embodiments, the block copolymers have molecular weights ranging from about 2,000 to about 1,000,000 Daltons, more particularly at least about 10,000 Daltons, and even more specifically at least about 25,000 Daltons or even at least about 50,000 Daltons. In a preferred embodiment, the block copolymers have a molecular weight between about 5,000 Daltons and about 30,000 Daltons. Number-average molecular weight ($M_n$) may also vary, but will generally fall in the range of about 1,000 to about 400,000 Daltons, preferably from about 1,000 to about 100,000 Daltons and, even more preferably, from about 1,000 to about 70,000 Daltons. Most preferably, $M_n$ varies between about 5,000 and about 300,000 Daltons.

The molecular weight of the inverse thermosensitive polymers is preferably between 1,000 and 50,000, more preferably between 5,000 and 35,000. Preferably the polymer is in an aqueous solution. For example, typical aqueous solutions contain about 5% to about 30% polymer, preferably about 10% to about 25%. The molecular weight of a suitable inverse thermosensitive polymers (such as a poloxamer or poloxamine) may be, for example, between 5,000 and 25,000, and more particularly between 7,000 and 20,000.

The pH of the inverse thermosensitive polymers formulation administered to a mammal is, generally, about 6.0 to about 7.8, which are suitable pH levels for injection into the mammalian body. The pH level may be adjusted by any suitable acid or base, such as hydrochloric acid or sodium hydroxide.

In certain embodiments, the inverse thermosensitive polymers of the invention are poloxamers or poloxamines. Pluronic® polymers have unique surfactant abilities and extremely low toxicity and immunogenic responses. These products have low acute oral and dermal toxicity and low potential for causing irritation or sensitization, and the general chronic and sub-chronic toxicity is low. In fact, Pluronic® polymers are among a small number of surfactants that have been approved by the FDA for direct use in medical applications and as food additives (BASF (1990) Pluronic® & Tetronic® Surfactants, BASF Co., Mount Olive, N.J.). Recently, several Pluronic® polymers have been found to enhance the therapeutic effect of drugs, and the gene transfer efficiency mediated by adenovirus. (March K L, Madison J E, Trapnell B C. "Pharmacokinetics of adenoviral vector-mediated gene delivery to vascular smooth muscle cells: modulation by poloxamer 407 and implication for cardiovascular gene therapy," *Hum Gene Therapy* 1995, 6, 41-53).

Interestingly, poloxamers (or Pluronics), as nonionic surfactants, are widely used in diverse industrial applications. (Nonionic Surfactants: polyoxyalkylene block copolymers, Vol. 60. Nace V M, Dekker M (editors), New York, 1996. 280 pp.) Their surfactant properties have been useful in detergency, dispersion, stabilization, foaming, and emulsification. (Cabana A, Abdellatif A K, Juhasz J. "Study of the gelation process of polyethylene oxide. polypropylene oxide-polyethylene oxide copolymer (poloxamer 407) aqueous solutions," *Journal of Colloid and Interface Science* 1997, 190, 307-312.) Certain poloxamines, e.g., poloxamine 1307 and 1107, also display inverse thermosensitivity.

Importantly, several members of this class of polymer (e.g., poloxamer 188, poloxamer 407, poloxamer 338, poloxamines 1107 and 1307) show inverse thermosensitivity within the physiological temperature range. (Qiu Y, Park K. "Environment-sensitive hydrogels for drug delivery," *Adv. Drug Deliv. Rev.* 2001, 53(3), 321-339; and Ron E S, Bromberg L E Temperature-responsive gels and thermogelling polymer matrices for protein and peptide delivery," Adv. Drug Deliv Rev. 1998, 31(3), 197-221.) In other words, these polymers are members of a class that are soluble in aqueous solutions at low temperature, but gel at higher temperatures. Poloxamer 407 is a biocompatible polyoxypropylene-polyoxyethylene block copolymer having an average molecular weight of about 12,500 and a polyoxypropylene fraction of about 30%; poloxamer 188 has an average molecular weight of about 8400 and a polyoxypropylene fraction of about 20%; poloxamer 338 has an average molecular weight of about 14,600 and a polyoxypropylene fraction of about 20%; poloxamine 1107 has an average molecular weight of about 14,000, poloxamine 1307 has an average molecular weight of about 18,000. Polymers of this type are also referred to as reversibly gelling because their viscosity increases and decreases with an increase and decrease in temperature, respectively. Such reversibly gelling systems are useful wherever it is desirable to handle a material in a fluid state, but performance is preferably in a gelled or more viscous state. As noted above, certain poly(ethyleneoxide)/poly(propyleneoxide) block copolymers have these properties; they are available commercially as Pluronic® poloxamers and Tetronic® poloxamines (BASF, Ludwigshafen, Germany) and generically known as poloxamers and poloxamines, respectively. (See U.S. Pat. Nos. 4,188,373, 4,478,822 and 4,474,751; all of which are incorporated by reference).

The average molecular weights of commercially available poloxamers and poloxamines range from about 1,000 to greater than 16,000 Daltons. Because the poloxamers are products of a sequential series of reactions, the molecular weights of the individual poloxamer molecules form a statistical distribution about the average molecular weight. In addition, commercially available poloxamers contain substantial amounts of poly(oxyethylene) homopolymer and poly(oxyethylene)/poly(oxypropylene) diblock polymers. The relative amounts of these byproducts increase as the molecular weights of the component blocks of the poloxamer increase. Depending upon the manufacturer, these byproducts may constitute from about 15% to about 50% of the total mass of the commercial polymer.

Purification of Inverse Thermosensitive Polymers

The inverse thermosensitive polymers may be purified using a process for the fractionation of water-soluble polymers, comprising the steps of dissolving a known amount of the polymer in water, adding a soluble extraction salt to the polymer solution, maintaining the solution at a constant optimal temperature for a period of time adequate for two distinct phases to appear, and separating physically the phases. Additionally, the phase containing the polymer fraction of the preferred molecular weight may be diluted to the original volume with water, extraction salt may be added to achieve the original concentration, and the separation process repeated as needed until a polymer having a narrower molecular weight distribution than the starting material and optimal physical characteristics can be recovered.

In certain embodiments, a purified poloxamer or poloxamine has a polydispersity index from about 1.5 to about 1.0. In certain embodiments, a purified poloxamer or poloxamine has a polydispersity index from about 1.2 to about 1.0.

The aforementioned process consists of forming an aqueous two-phase system composed of the polymer and an appropriate salt in water. In such a system, a soluble salt can be added to a single phase polymer-water system to induce phase separation to yield a high salt, low polymer bottom phase, and a low salt, high polymer upper phase. Lower molecular weight polymers partition preferentially into the high salt, low polymer phase. Polymers that can be fractionated using this process include polyethers, glycols such as poly(ethylene glycol) and poly(ethylene oxide)s, polyoxyalkylene block copolymers such as poloxamers, poloxamines, and polyoxypropylene/polyoxybutylene copolymers, and other polyols, such as polyvinyl alcohol. The average molecular weight of these polymers may range from about 800 to greater than 100,000 Daltons. See U.S. Pat. No. 6,761,824; hereby incorporated by reference. The aforementioned purification process inherently exploits the differences in size and polarity, and therefore solubility, among the poloxamer molecules, the poly(oxyethylene) homopolymer and the poly(oxyethylene)/poly(oxypropylene) diblock byproducts. The polar fraction of the poloxamer, which generally includes the lower molecular weight fraction and the byproducts, is removed allowing the higher molecular weight fraction of poloxamer to be recovered. The larger molecular weight poloxamer recovered by this method has physical characteristics substantially different from the starting material or commercially available poloxamer including a higher average molecular weight, lower polydispersity and a higher viscosity in aqueous solution.

Other purification methods may be used to achieve the desired outcome. For example, WO 92/16484 discloses the use of gel permeation chromatography to isolate a fraction of poloxamer 188 that exhibits beneficial biological effects, without causing potentially deleterious side effects. The copolymer thus obtained had a polydispersity index of 1.07 or less, and was substantially saturated. The potentially harmful side effects were shown to be associated with the low molecular weight, unsaturated portion of the polymer, while the medically beneficial effects resided in the uniform higher molecular weight material. Other similarly improved copolymers were obtained by purifying either the polyoxypropylene center block during synthesis of the copolymer, or the copolymer product itself (e.g., U.S. Pat. Nos. 5,523,492 and 5,696,298; both of which are herein incorporated by reference).

Further, a supercritical fluid extraction technique has been used to fractionate a polyoxyalkylene block copolymer as disclosed in U.S. Pat. No. 5,567,859 (hereby incorporated by reference). A purified fraction was obtained, which was composed of a fairly uniform polyoxyalkylene block copolymer having a polydispersity of less than 1.17. According to this method, the lower molecular weight fraction was removed in a stream of carbon dioxide maintained at a pressure of 2200 pounds per square inch (psi) and a temperature of 40° C.

Additionally, U.S. Pat. No. 5,800,711 (hereby incorporated by reference) discloses a process for the fractionation of polyoxyalkylene block copolymers by the batchwise removal of low molecular weight species using a salt extraction and liquid phase separation technique. Poloxamer 407 and poloxamer 188 were fractionated by this method. In each case, a copolymer fraction was obtained which had a higher average molecular weight and a lower polydispersity index as compared to the starting material. However, the changes in polydispersity index were modest and analysis by gel permeation chromatography indicated that some low-molecular-weight material remained. The viscosity of aqueous solutions of the fractionated polymers was significantly greater than the viscosity of the commercially available polymers at temperatures between 10° C. and 37° C., an important property for some medical and drug delivery applications. Nevertheless, some of the low molecular weight contaminants of these polymers are thought to cause deleterious side effects when used inside the body, making it especially important that they be removed in the fractionation process. As a consequence, polyoxyalkylene block copolymers fractionated by this process are not appropriate for all medical uses.

Selected Balloons and Skirts of the Invention

Balloon and skirts of the invention can be of various shapes and sizes (for example, those shown in FIGS. 3-6) and can be formed from a variety of polymers and polymer combinations. For example, elastomers, such as thermoplastic elastomers and engineering thermoplastic elastomers, such as polybutylene terephthalate-polyethene glycol block copolymers, which are available, for example, as HYTREL®, can be used. These are discussed in U.S. Pat. No. 5,797,877, which is incorporated herein by reference. Other polymers which may be used include polyurethenes. Other polymers include copolymers such as ABS (acrylonitrile-butadiene-styrene), ABS/nylon, ABS/polyvinyl chloride (PVC), ABS/polycarbonate, acrylonitrile copolymer, polyacrylamide, polyacrylate and polyacrylsulfone, polyesters such as polyethylene terephthalate (PET), polybutylene terephthalate (PBT), polyethylene naphthalate (PEN), liquid crystal polymer (LCP), polyester/polycaprolactone and polyester/polyadipate; and high melt temperature polyethers including polyetheretherketone (PEEK), polyethersulfone (PES), polyetherimide (PEI) and polyetherketone (PEK), polymenthylpentene, polyphenylene ether, polyphenylene sulfide, and styrene acrylonitrile (SAN), polyamides such as nylon 6, nylon 6/6, nylon 6/66, nylon 6/9, nylon 6/10, nylon 6/12, nylon 11, nylon 12, ethylene, propylene ethylene vinylacetate and ethylene vinyl alcohol (EVA), various ionomers, polyethylene type I-IV, polyolefins, polyurethane, polyvinyl chloride, and polysiloxanes (silicones). In addition fluorocarbons such as polychlorotriethylene (CTFE), poly[ethylene-co-chlorotrifluoroethylene] (ECTFE) copolymer ethylene tetrafluoroethylene (ETFE), copolymer tetrafluoroethylene and hexafluoropropylene (FEP), perfluoroalkane (PFA) and poly[vinylidene fluoride] (PVDF) can be used. Other polymers suitable for use in the balloons of the invention are described in U.S. Patent Applications Publication Nos. 2006/0182913 and 2006/0184112, both of which are hereby incorporated by reference.

In certain embodiments, the balloons and skirts of the invention have a minimum wall thickness of at least about 1 micron (e.g., at least about 1.5 micron, at least about 2 micron, at least about 2.5 micron, at least about 3.0 microns, at least about 3.5 microns), and/or a maximum thickness of at most about 100 microns (e.g., at most about 5 microns, at most about 10 microns, at most about 20 microns, at most about 25 microns, at most about 30 microns, at most about 40 microns, at most about 45 microns, at most about 50 microns, at most about 60 microns, at most about 70 microns, at most about 80 microns, at most about 90 microns).

In certain embodiments, a balloon of the invention has a burst pressure of at least about 0.5 to 10 atm (e.g., about 10 atm of greater). In certain embodiments, a balloon of the invention has a burst pressure of up to about 30 atm or up to about 40 atm. As referred to herein, the burst pressure of a balloon refers to the internal pressure at which the balloon bursts. One way the burst pressure of a balloon is determined is by measuring the internal pressure of the balloon as the balloon is inflated at a rate of two psi per second with a 10 second hold at every 50 psi interval until the balloon bursts.

Selected Methods of the Invention

In certain embodiments, the invention relates to polymer-filled balloons or skirts, and catheters using such balloons or skirts, for administering treatments to widen constricted passages in, for example, angioplasty, valvuloplasty, or urological procedures. In other embodiments, the invention relates to the use of polymer-filled balloons or skirts to prevent the flow of fluids through bodily passageways. In certain embodiments the polymer-filled balloons or skirts can be punctured or inverted, respectively, allowing the contained polymer to be dissolved in the surrounding bodily fluid or irrigation fluid. In certain embodiments, saline or cold saline can be used to dissolve the gelled polymer.

One aspect of the invention relates to a method of occluding, widening or stenting a lumen in a mammal, comprising the steps of:

positioning a catheter into said mammalian lumen at a location, wherein said catheter comprises an elongated shaft having an inflation lumen and a balloon or skirt connected to the elongated shaft so that an interior chamber of the balloon or skirt is in fluid communication with the inflation lumen;

filling said balloon or skirt, via said inflation lumen, with a composition comprising at least one polymer, wherein said composition gels partially or completely in said balloon or skirt.

In certain embodiments, the present invention relates to the aforementioned method, wherein said catheter comprises a balloon.

In certain embodiments, the present invention relates to the aforementioned method, wherein said catheter comprises a skirt.

In certain embodiments, the present invention relates to the aforementioned method, wherein said method is substantially atraumatic to said mammalian lumen.

In certain embodiments, the present invention relates to the aforementioned method, wherein said mammalian lumen is temporarily occluded.

In certain embodiments, the present invention relates to the aforementioned method, wherein said mammalian lumen is permanently occluded.

In certain embodiments, the present invention relates to the aforementioned method, wherein said catheter further comprises a guidewire lumen.

In certain embodiments, the present invention relates to the aforementioned method, wherein said catheter is a stent delivery catheter with a stent mounted on the balloon or skirt.

In certain embodiments, the present invention relates to the aforementioned method, wherein said catheter is a stent delivery catheter with a stent mounted on the balloon or skirt; and the stent carries a therapeutic agent.

In certain embodiments, the present invention relates to the aforementioned method, wherein said at least one polymer is at least one optionally purified inverse thermosensitive polymer.

In certain embodiments, the present invention relates to the aforementioned method, wherein said at least one polymer is at least one purified inverse thermosensitive polymer.

In certain embodiments, the present invention relates to the aforementioned method, wherein said composition has a transition temperature of between about 10° C. and about 40° C.

In certain embodiments, the present invention relates to the aforementioned method, wherein said composition has a transition temperature of between about 15° C. and about 30° C.

In certain embodiments, the present invention relates to the aforementioned method, wherein said composition has a transition temperature of about 25° C.

In certain embodiments, the present invention relates to the aforementioned method, wherein said composition gels over a temperature range of about 2° C. to about 5° C.

In certain embodiments, the present invention relates to the aforementioned method, wherein said composition gels over a temperature range of about 2° C. to about 3° C.

In certain embodiments, the present invention relates to the aforementioned method, wherein said composition gels over a temperature range of about 2° C.

In certain embodiments, the present invention relates to the aforementioned method, wherein said optionally purified inverse thermosensitive polymer has a polydispersity index from about 1.5 to about 1.0.

In certain embodiments, the present invention relates to the aforementioned method, wherein said optionally purified inverse thermosensitive polymer has a polydispersity index from about 1.2 to about 1.0.

In certain embodiments, the present invention relates to the aforementioned method, wherein said optionally purified inverse thermosensitive polymer has a polydispersity index from about 1.1 to about 1.0.

In certain embodiments, the present invention relates to the aforementioned method, wherein said optionally purified inverse thermosensitive polymer is selected from the group consisting of block copolymers, random copolymers, graft polymers, and branched copolymers.

In certain embodiments, the present invention relates to the aforementioned method, wherein said optionally purified inverse thermosensitive polymer is a polyoxyalkylene block copolymer.

In certain embodiments, the present invention relates to the aforementioned method, wherein said optionally purified inverse thermosensitive polymer is selected from the group consisting of poloxamers and poloxamines.

In certain embodiments, the present invention relates to the aforementioned method, wherein said optionally purified inverse thermosensitive polymer is selected from the group consisting of poloxamer 407, poloxamer 338, poloxamer 118, Tetronic® 1107 and Tetronic® 1307.

In certain embodiments, the present invention relates to the aforementioned method, wherein said optionally purified inverse thermosensitive polymer is poloxamer 407.

In certain embodiments, the present invention relates to the aforementioned method, wherein said optionally purified inverse thermosensitive polymer is a poloxamer or poloxamine; and said composition has a transition temperature of between about 10° C. and 40° C.

In certain embodiments, the present invention relates to the aforementioned method, wherein said optionally purified inverse thermosensitive polymer is a poloxamer or poloxamine; and said composition has a transition temperature of between about 15° C. and 30° C.

In certain embodiments, the present invention relates to the aforementioned method, wherein said optionally purified inverse thermosensitive polymer is a poloxamer or poloxamine; and said composition has a transition temperature of about 25° C.

In certain embodiments, the present invention relates to the aforementioned method, wherein said composition comprises about 5% to about 35% of said optionally purified inverse thermosensitive polymer.

In certain embodiments, the present invention relates to the aforementioned method, wherein said composition comprises about 10% to about 30% of said optionally purified inverse thermosensitive polymer.

In certain embodiments, the present invention relates to the aforementioned method, wherein said composition comprising at least one polymer comprises an anionic, cationic, or non-ionically crosslinkable polymer.

In certain embodiments, the present invention relates to the aforementioned method, wherein said composition comprising at least one polymer comprises a polymer selected from the group consisting of alginic acid, sodium alginate, potassium alginate, sodium gellan, potassium gellan, carboxy methyl cellulose, hyaluronic acid and polyvinyl alcohol.

In certain embodiments, the present invention relates to the aforementioned method, wherein said composition comprising at least one polymer further comprises phosphate, citrate, borate, succinate, maleate, adipate, oxalate, calcium, magnesium, barium, strontium, or a combination thereof.

In certain embodiments, the present invention relates to the aforementioned method, wherein said composition comprising at least one polymer comprises a polymer selected from the group consisting of alginic acid, sodium alginate, potassium alginate, sodium gellan and potassium gellan; and said composition comprising at least one polymer further comprises calcium, magnesium or barium.

In certain embodiments, the present invention relates to the aforementioned method, wherein said composition comprising at least one polymer comprises a polymer selected from the group consisting of alginic acid, sodium alginate or potassium alginate; and said composition comprising at least one polymer further comprises calcium.

In certain embodiments, the present invention relates to the aforementioned method, wherein said composition comprising at least one polymer comprises a polymer selected from the group consisting of sodium gellan and potassium gellan; and said composition comprising at least one polymer further comprises magnesium.

In certain embodiments, the present invention relates to the aforementioned method, wherein said composition comprising at least one polymer comprises hyaluronic acid; and said composition comprising at least one polymer further comprises calcium.

In certain embodiments, the present invention relates to the aforementioned method, wherein said composition comprising at least one polymer comprises polyvinyl alcohol; and said composition comprising at least one polymer further comprises borate.

In certain embodiments, the present invention relates to the aforementioned method, wherein the volume of said composition at physiological temperature is about 80% to about 120% of its volume below its transition temperature.

In certain embodiments, the present invention relates to the aforementioned method, wherein said composition further comprises a contrast-enhancing agent.

In certain embodiments, the present invention relates to the aforementioned method, wherein said contrast-enhancing agent is selected from the group consisting of radiopaque materials, paramagnetic materials, heavy atoms, transition metals, lanthanides, actinides, dyes, and radionuclide-containing materials.

In certain embodiments, the present invention relates to the aforementioned method, wherein said mammal is a human.

In certain embodiments, the present invention relates to the aforementioned method, wherein said mammalian lumen is an artery, a vein, a kidney, a gall bladder, a ureter, a urinary bladder, a pancreatic duct, a fallopian tube, a sinus, a tear duct, a salivary gland, lumens or other cavities of the lymphatic system, a colon, a small intestine or a large intestine.

In certain embodiments, the present invention relates to the aforementioned method, wherein said mammalian lumen is an artery.

In certain embodiments, the present invention relates to the aforementioned method, wherein said mammalian lumen is a gun shot wound or a laceration.

In certain embodiments, the present invention relates to the aforementioned method, wherein said mammalian lumen is calcified.

In certain embodiments, the present invention relates to the aforementioned method, wherein said mammalian lumen is occluded for diagnostic purposes.

In certain embodiments, the present invention relates to the aforementioned method, wherein said mammalian lumen is occluded for therapeutic purposes.

In certain embodiments, the present invention relates to the aforementioned method, further comprising the step of cooling said location, thereby liquefying the gel in said balloon or skirt.

In certain embodiments, the present invention relates to the aforementioned method, wherein said location is cooled by using a cold aqueous solution or ice.

In certain embodiments, the present invention relates to the aforementioned method, further comprising the step of injecting an aqueous solution into said balloon or skirt, thereby dissolving said gel in said balloon or skirt.

In certain embodiments, the present invention relates to the aforementioned method, further comprising the step of injecting an aqueous solution into said balloon or skirt, thereby dissolving said gel in said balloon or skirt.

In certain embodiments, the present invention relates to the aforementioned method, further comprising the step of piercing the balloon or inverting the skirt to allow release of the polymer composition contained within, thereby dissolving it in the surrounding bodily fluid.

In certain embodiments, the present invention relates to the aforementioned method, further comprising the steps of piercing the balloon or inverting the skirt to allow release of the polymer composition contained within; and injecting saline into said balloon or skirt, thereby dissolving the polymer composition.

In certain embodiments, the present invention relates to the aforementioned method, wherein the temperature of said saline is below 25° C.

In certain embodiments, the present invention relates to the aforementioned method, wherein said skirt is a convex skirt.

In certain embodiments, the present invention relates to the aforementioned method, further comprising the step of pulling the catheter shaft to cause inversion of the skirt and dissolution of the gel.

In certain embodiments, the present invention relates to the aforementioned method, wherein said skirt is a concave skirt.

In certain embodiments, the present invention relates to the aforementioned method, further comprising the step of pushing the catheter shaft to cause inversion of the skirt and dissolution of the gel.

In certain embodiments, the present invention relates to the aforementioned method, wherein said method is part of a surgical procedure; and said location is a surgical site.

In certain embodiments, the present invention relates to the aforementioned method, wherein said surgical site is at or proximal to a hemorrhage, cancerous tissue, tumor, or organ.

In certain embodiments, the present invention relates to the aforementioned method, wherein said surgical procedure comprises anastomosis.

In certain embodiments, the present invention relates to the aforementioned method, wherein said anastomosis comprises connecting a first vessel and a second vessel.

In certain embodiments, the present invention relates to the aforementioned method, wherein said connecting a first vessel and a second vessel comprises suturing, laser welding or laser soldering.

In certain embodiments, the present invention relates to the aforementioned method, wherein said anastomosis is selected from the group consisting of end-to-end anastomosis, side-to-end anastomosis and side-to-side anastomosis.

In certain embodiments, the present invention relates to the aforementioned method, wherein said occlusion reduces bleeding during said surgical procedure.

In certain embodiments, the present invention relates to the aforementioned method, wherein said occlusion enables controlled ischemic preconditioning of said surgical site.

In certain embodiments, the present invention relates to the aforementioned method, wherein said occlusion is at or proximal to an incision site for minimally invasive surgery and decreases bleeding through the incision.

In certain embodiments, the present invention relates to the aforementioned method, wherein said balloon is a standard balloon, a conical balloon, a square balloon, a spherical balloon, a conical/square balloon, a long conical/square balloon, a conical/spherical balloon, a long spherical balloon, a tapered balloon, a dog bone balloon, a stepped balloon, an offset balloon, or a conical/offset balloon.

In certain embodiments, the present invention relates to the aforementioned method, wherein said balloon or skirt is formed from a polymer selected from the group consisting of polybutylene terephthalate-polyethene glycol block copolymers, polyurethenes, ABS (acrylonitrile-butadiene-styrene), ABS/nylon, ABS/polyvinyl chloride (PVC), ABS/polycarbonate, acrylonitrile copolymer, polyacrylamide, polyacrylate, polyacrylsulfone, polyesters, polyethylene terephthalate (PET), polybutylene terephthalate (PBT), polyethylene naphthalate (PEN), liquid crystal polymer (LCP), polyester/polycaprolactone, polyester/polyadipate, polyetheretherketone (PEEK), polyethersulfone (PES), polyetherimide (PEI), polyetherketone (PEK), polymenthylpentene, polyphenylene ether, polyphenylene sulfide, styrene acrylonitrile (SAN), polyamides, nylon 6, nylon 6/6, nylon 6/66, nylon 6/9, nylon 6/10, nylon 6/12, nylon 11, nylon 12, ethylene, propylene ethylene vinylacetate, ethylene vinyl alcohol (EVA), ionomers, polyethylene type I-IV, polyolefins, polyurethane, polyvinyl chloride, polysiloxanes (silicones), fluorocarbons, polychlorotriethylene (CTFE), poly[ethylene-co-chlorotrifluoroethylene] (ECTFE) copolymer ethylene tetrafluoroethylene (ETFE), copolymers of tetrafluoroethylene and hexafluoropropylene (FEP), perfluoroalkane (PFA) and poly[vinylidene fluoride] (PVDF).

In certain embodiments, the present invention relates to the aforementioned method, wherein said balloon or skirt has a wall thickness of between about 1 micron and about 20 microns.

In certain embodiments, the present invention relates to the aforementioned method, wherein said balloon has a burst pressure of between about 0.5 atm and about 30 atm.

In certain embodiments, the present invention relates to the aforementioned method, wherein said balloon substantially conforms to the shape of the mammalian lumen.

In certain embodiments, the present invention relates to the aforementioned method, wherein said balloon is filled to a pressure.

In certain embodiments, the present invention relates to the aforementioned method, wherein said pressure is between about 1 atm and about 20 atm.

In certain embodiments, the present invention relates to the aforementioned method, wherein said pressure is between about 1 atm and about 15 atm.

In certain embodiments, the present invention relates to the aforementioned method, wherein said pressure is between about 1 atm and about 10 atm.

In certain embodiments, the present invention relates to the aforementioned method, wherein said pressure is between about 1 atm and about 5 atm.

EXEMPLIFICATION

The invention now being generally described, it will be more readily understood by reference to the following examples, which are included merely for purposes of illustration of certain aspects and embodiments of the present invention, and are not intended to limit the invention.

Example 1

Purification of Poloxamer 407

Poloxamer 407 (486.0 g, lot number WPHT-543B), purchased from BASF Corporation, Mount Olive, N.J., was dissolved in deionized water (15,733 g). The solution was maintained at 0.1° C. and 2335.1 g of $(NH_4)_2SO_4$ were added. The solution was equilibrated at 2° C. and after two distinct phases formed, the lower phase was discarded, and the upper phase (2060 g) was collected and weighed. Deionized water (14159 g) was added and the solution was equilibrated to 2° C. Next, 2171.6 g of $(NH_4)_2SO_4$ were added with stirring. After the salt was dissolved, the solution was maintained at approximately 2° C. until two phases formed. The upper phase (3340 g) was isolated and diluted with 12879 g of deionized water. The solution was chilled to about 2.2° C. and 2062 g of $(NH_4)_2SO_4$ were added. The phases were allowed to separate as above. The upper phase was isolated and extracted with 4 liters of dichloromethane. Two phases were allowed to form overnight. The organic (lower) phase was isolated and approximately 2 kg of sodium sulfate $(Na_2SO_4)$ were added to it to remove the remaining water. The dichloromethane phase was filtered through a PTFE filter (0.45 μm pore size) to remove the undissolved salts. The dichloromethane was removed under vacuum at approximately 30° C. Final traces of dichloromethane were removed by drying in an oven overnight at about 30° C. A total of 297.6 g of fractionated poloxamer 407 (lot number 00115001) were recovered. The chemical and physical characteristics of the fractionated poloxamer 407 are compared to those of the starting material in FIG. 2[A].

Example 2

Gelation Temperature of Selected Reverse Phase Media

The optionally-purified polymer was weighed into a plastic tube. To achieve the required concentration the weight was multiplied by 4, for 25 weight percent (w %), and by 5, for 20 weight percent (w %), and the required final weight was achieved by adding saline. The solutions were placed in the fridge at 4° C. and usually were ready within 24 hours. Gelation points were measured in a Brookfield viscometer and the point at which viscosity exceeded the range of the plate/cone (greater than about 102,000 cP) was called the gelation temperature. Results are shown in FIG. 2[B].

INCORPORATION BY REFERENCE

U.S. patent Application 2005/0147585 is hereby incorporated by reference in its entirety. U.S. Pat. No. 4,708,140 is hereby incorporated by reference in its entirety. In addition, all of the U.S. Patents and U.S. Published Patent Applications cited herein are hereby incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A method of occluding, widening or stenting a lumen in a mammal, comprising the steps of:
    positioning a catheter into said mammalian lumen at an location, wherein said catheter comprises an elongated shaft having an inflation lumen and a skirt connected to a distal end of the elongated shaft so that an interior chamber of the skirt is in fluid communication with the inflation lumen; and wherein an open proximal end of the skirt is in fluid communication with said mammalian lumen;
    deploying said skirt, via said inflation lumen, with a composition comprising at least one polymer by introducing the composition in a manner sufficient to expand the skirt, wherein said composition gels partially or completely in said skirt.

2. The method of claim 1, wherein said method is substantially atraumatic to said mammalian lumen.

3. The method of claim 1, wherein said mammalian lumen is temporarily occluded.

4. The method of claim 1, wherein said mammalian lumen is permanently occluded.

5. The method of claim 1, wherein said at least one polymer is at least one purified inverse thermosensitive polymer.

6. The method of claim 5, wherein said purified inverse thermosensitive polymer has a polydispersity index from about 1.5 to about 1.0.

7. The method of claim 5, wherein said purified inverse thermosensitive polymer has a polydispersity index from about 1.2 to about 1.0.

8. The method of claim 5, wherein said purified inverse thermosensitive polymer has a polydispersity index from about 1.1 to about 1.0.

9. The method of claim 5, wherein said purified inverse thermosensitive polymer is a polyoxyalkylene block copolymer.

10. The method of claim 5, wherein said purified inverse thermosensitive polymer is selected from the group consisting of poloxamers and poloxamines.

11. The method of claim 5, wherein said purified inverse thermosensitive polymer is selected from the group consisting of poloxamer 407, poloxamer 338, poloxamer 118, poloxamine 1107 and poloxamine 1307.

12. The method of claim 5, wherein said purified inverse thermosensitive polymer is poloxamer 407.

13. The method of claim 1, wherein said mammal is a human.

14. The method of claim 1, wherein said mammalian lumen is an artery, a vein, a kidney, a gall bladder, a ureter, a urinary bladder, a pancreatic duct, a fallopian tube, a sinus, a tear duct, a salivary gland, lumens or other cavities of the lymphatic system, a colon, a small intestine or a large intestine.

15. The method of claim 1, wherein said mammalian lumen is an artery.

16. The method of claim 1, wherein said mammalian lumen is a gun shot wound or a laceration.

17. The method of claim 1, wherein said mammalian lumen is calcified.

18. The method of claim 1, wherein said method is part of a surgical procedure; and said location is a surgical site.

19. The method of claim 18, wherein said surgical site is at or proximal to a hemorrhage, cancerous tissue, tumor, or organ.

20. The method of claim 18, wherein said surgical procedure comprises anastomosis.

21. The method of claim 20, wherein said anastomosis is selected from the group consisting of end-to-end anastomosis, side-to-end anastomosis and side-to-side anastomosis.

22. The method of claim 1, wherein said skirt is formed from a polymer selected from the group consisting of polybutylene terephthalate-polyethene glycol block copolymers, polyurethenes, ABS (acrylonitrile-butadiene-styrene), ABS/nylon, ABS/polyvinyl chloride (PVC), ABS/polycarbonate, acrylonitrile copolymer, polyacrylamide, polyacrylate, polyacrylsulfone, polyesters, polyethylene terephthalate (PET), polybutylene terephthalate (PBT), polyethylene naphthalate (PEN), liquid crystal polymer (LCP), polyester/polycaprolactone, polyester/polyadipate, polyetheretherketone (PEEK), polyethersulfone (PES), polyetherimide (PEI), polyetherketone (PEK), polymenthylpentene, polyphenylene ether, polyphenylene sulfide, styrene acrylonitrile (SAN), polyamides, nylon 6, nylon 6/6, nylon 6/66, nylon 6/9, nylon 6/10, nylon 6/12, nylon 11, nylon 12, ethylene, propylene ethylene vinylacetate, ethylene vinyl alcohol (EVA), ionomers, polyethylene type I-IV, polyolefins, polyurethane, polyvinyl chloride, polysiloxanes (silicones), fluorocarbons, polychlorotriethylene (CTFE), poly[ethylene-co-chlorotrifluoroethylene] (ECTFE) copolymer ethylene tetrafluoroethylene (ETFE), copolymers of tetrafluoroethylene and hexafluoropropylene (FEP), perfluoroalkane (PFA) and poly[vinylidene fluoride] (PVDF).

* * * * *